(12) United States Patent
Stenzel et al.

(10) Patent No.: US 6,235,281 B1
(45) Date of Patent: May 22, 2001

(54) USE OF ANTI-TNF ANTIBODIES AS DRUGS FOR THE TREATMENT OF DISORDERS WITH AN ELEVATED SERUM LEVEL OF INTERLEUKIN-6

(75) Inventors: Roswitha Stenzel, Lampertheim; Martin Kaul, Neustadt; Lothar Daum, Otterstadt; Joachim Kempeni, Neustadt; Christa Raab, Dannstadt-Schauernheim; Sibylle Schaefer, Walldorf, all of (DE)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/687,328

(22) PCT Filed: Jan. 27, 1995

(86) PCT No.: PCT/EP95/00291

§ 371 Date: Aug. 7, 1996

§ 102(e) Date: Aug. 7, 1996

(87) PCT Pub. No.: WO95/20978

PCT Pub. Date: Aug. 10, 1995

(30) Foreign Application Priority Data

Feb. 7, 1994 (DE) .................................. 44 03 669
Mar. 19, 1994 (DE) .................................. 44 09 513

(51) Int. Cl.$^7$ .......................... A61K 39/395; A61K 38/02
(52) U.S. Cl. ..................... 424/145.1; 424/142.1; 424/1.41; 424/154.1; 514/2; 514/12; 530/350; 530/388.1; 530/388.15; 530/388.23; 530/389.2

(58) Field of Search .................. 424/133.1, 141.1, 424/145.1, 154.1, 142.1; 514/2, 12; 530/387.3, 388.1, 388.23, 350, 388.15, 389.2

(56) References Cited

U.S. PATENT DOCUMENTS 5,183,657 * 2/1993 Buurman et al. .................. 424/85.8
5,231,024 * 7/1993 Moeller et al. ................. 435/240.27

FOREIGN PATENT DOCUMENTS

0526905 * 2/1993 (EP) .
91/03553 * 3/1991 (WO) .
9306213 * 4/1993 (WO) .

OTHER PUBLICATIONS

Fisher et al Critical Care Medicine 21(3): 318–326, Mar., 1993.*
Engelberts et al. Lymphokine & Cytokine Res. 10(2): 127–131, 1991.*
Damas et al Am Surg 215(4): 356–362, 1992.*
Hinshaw et al Circulatory Shock 30: 279–292, 1990.*
Tracey et al Nature 330:662–664, 1987.*
Stephenson JAMA vol. 275 No. 11 pp 823–824, 1996.*
Rhein R. Biotechnology Monday Oct. 4, 1993.*
Natanson et al Annals of Internal Med. 120 (9):771–783, 1994.*

* cited by examiner

*Primary Examiner*—Nancy A Johnson
(74) *Attorney, Agent, or Firm*—Oblon, Spivak, McClelland, Maier & Neustadt, P.C.

(57) ABSTRACT

The invention relates to the use of TNF antagonists for producing drugs for the treatment of disorders characterized by elevated serum levels of interleukin-6.

4 Claims, 2 Drawing Sheets

USE OF ANTI-TNF ANTIBODIES AS DRUGS FOR THE TREATMENT OF DISORDERS WITH AN ELEVATED SERUM LEVEL OF INTERLEUKIN-6

BACKGROUND OF THE INVENTION FIELD OF THE INVENTION

The present invention relates to the use of anti-TNF antibodies in the treatment of disorders with an elevated serum level of interleukin-6.

DISCUSSION OF THE BACKGROUND

It is known that the term tumor necrosis factor (TNF) embraces two cytotoxic factors (TNF-α and TNF-β) which are mostly produced by activated lymphocytes and monocytes.

EP 260 610 describes, for example, anti-TNF antibodies which are said to be utilizable for disorders associated with an increased level of TNF in the blood, such as septic shock, transplant rejection, allergies, autoimmune diseases, shock lung, coagulation disturbances or inflammatory bone diseases, to inactivate TNF.

Examples of disorders characterized by elevated serum levels of interleukin-6 in patients are the sequelae of transplantations, autoimmune diseases and, in particular, certain types of septicemia.

Septicemia is defined in medical textbooks as a collective clinical term for conditions in which bacterial pathogens, starting from a focus, enter the blood stream to induce a wide range of subjective and objective pathological manifestations. It is furthermore found that the clinical picture may vary widely depending on the type of pathogen, the reactivity of the body, the primary focus and the changes in organ involvement (Sturm et al. "Grundbegriffe der Inneren Medizin", 13th edition, page 570, Gustav Fischer Verlag, Stuttgart, 1984).

A number of cytokines have been suggested to be involved in the complex pathophysiological process of septicemia. TNF in particular is ascribed with an important role in septic shock on the basis of data from animal experiments (Beutler et al., Science 229 (1985) 869–871).

This has eventually led to clinical studies of the treatment of septicemic patients with anti-TNF antibodies.

In a recently published multicenter phase II study on the treatment of severe septicemia with a murine monoclonal anti-TNF antibody, however, it was found that the overall population (80 patients) did not profit in terms of survival rate from the treatment with the antibody. Only the patients with elevated circulating TNF concentrations appeared to profit, in terms of probability of survival, from high-dose anti-TNF antibody administration (C. J. Fisher et al., Critical Care Medicine, vol. 21, No. 3, pages 318–327). Furthermore, reference is made in this study to a correlation of the plasma levels of TNF and Il-6.

The part played by the cytokine interleukin-6 (Il-6) in septicemia is unclear and contradictory. Elevated serum levels of Il-6 have been found in some septicemic patients (Hack et al., Blood 74 (1989) 1704–1710).

Waage describes a correlation between the concentrations of the cytokines Il-6 and Il-8 with the severity of the shock, although they had no effect, either alone or in combination with TNF, on the development of a shock syndrome in terms of mortality (Waage in "Tumor Necrosis Factors", ed. B. Beutler, Raven Press, New York, 1992, pages 275–283).

Some scientists have ascribed a beneficial role to Il-6 in septic shock because Il-6 inhibits, in the form of negative feedback control, the LPS-induced TNF production (Libert et al. in "Tumor Necrosis Factor: Molecular and Cellular Biology and Clinical Relevance", ed. W. Fiers, Karger, Basel, 1993, pages 126–131).

SUMMARY OF THE INVENTION

We have now found, surprisingly, that TNF antagonists can be used particularly successfully as drugs for the treatment of disorders characterized by elevated serum levels of interleukin-6.

DESCRIPTION OF THE PREFERRED EMBODIMENTS

The treatment of septicemia with TNF antagonists is particularly successful according to this invention, for example measured by a distinct reduction in mortality, when the septicemic patients who are treated have Il-6 levels of 500 pg/ml or more at the start of treatment. Patients who have Il-6 serum levels above 1000 pg/ml profit particularly well from the treatment according to the invention.

Elevated serum levels of Il-6 mean levels which are elevated at least ten-fold compared with physiological serum levels in healthy subjects.

Serum concentrations of Il-6 up to 20,000 times the levels in healthy subjects have been found in septicemic patients.

The "normal" Il-6 serum levels are usually below the detection limit, which may vary slightly depending on the assay system used. Their maximum is, however, 20 pg/ml.

The serum concentrations of Il-6 can be determined by conventional detection methods such as RIA or ELISA. An example of a very suitable detection system is the Il-6-EASIA supplied by Medgenix.

The Il-6 concentration can also be determined by an activity assay in which, for example, C-reactive protein is assayed.

Suitable TNF antagonists are anti-TNF antibodies, TNF receptors and soluble fragments thereof, TNF binding proteins or those TNF derivatives which still bind to TNF receptors but have no TNF activity. TNF antagonists of these types have the characteristic that they trap TNF which has been formed and do not allow it to reach the TNF receptor or that they compete with TNF for the receptor.

However, TNF antagonists which prevent the formation or release of TNF are also suitable for the use according to the invention. Such substances inhibit for example TNF gene expression or release of TNF from precursor forms.

Such TNF-antagonistic activities have been described for example for xanthine derivatives, glucocorticoids, prostaglandin E2, thalidomide, interleukin-4, interleukin-10, granulocyte-stimulating factor (G-CSF), cyclosporin and α-antitrypsin. Hence compounds of these types are also suitable as TNF antagonists.

Anti-TNF antibodies are particularly preferred for the use according to the invention.

The anti-TNF antibodies suitable for the use according to the invention are known (EP 260 610, EP 351 789, EP 218 868). Both polyclonal and monoclonal antibodies can be used. Furthermore, TNF-binding antibody fragments such as Fab or F(ab')$_2$ fragments or single-chain Fv fragments are also suitable.

Furthermore, humanized or human anti-TNF antibodies or their TNF-binding fragments are also very suitable because these molecules ought not to cause any anti-mouse antigenicity in human patients.

It is also possible to use mixtures of various anti-TNF antibodies or of anti-TNF antibodies and TNF receptor fragments as active substance.

The present invention includes pharmaceutical compositions which, besides non-toxic, inert, pharmaceutically suitable vehicles, contain the anti-TNF antibodies, and processes for the production of these compositions.

The anti-TNF antibodies are formulated in the conventional way for biotechnologically produced active substances, as a rule as liquid formulation or lyophilisate (see, for example, Hagers Handbuch der pharmazeutischen Praxis, vol. 2, 5th edition, 1991, p. 720, ISBN 3-540-52459-2). The abovementioned pharmaceutical compositions are produced in a conventional way by conventional methods, eg. by mixing the active substance or substances with the vehicle or vehicles.

In general, it has proven advantageous to administer the active substance or substances which are suitable for the use according to the invention in total amounts of about 0.1 to about 1000, preferably 0.1 to 10, mg/kg of body weight every 24 hours, where appropriate in the form of several individual doses or as continuous infusion and, where appropriate, over a therapy period of several days to achieve the desired results. Administration can take place as brief intravenous infusion of the single doses or as continuous long-term infusion of the daily dose over 24 hours. A single dose preferably contains the active substance or substances in amounts of about 0.1 to about 10 mg/kg of body weight. However, it may be necessary to deviate from the stated dosages, specifically depending on the age and size of the patient to be treated and on the nature and severity of the fundamental disorder, the type of composition and of administration of the drug, and the period or interval over which administration takes place. The invention is illustrated further in the following Example.

EXAMPLE

Treatment of septicemic patients with a murine anti-TNF antibody fragment (F(ab')$_2$ ).

A total of 122 patients with severe septicemia were treated in a multicenter clinical study with anti-TNF antibody fragment in various dosages or with placebo.

The four therapeutic methods investigated differed only in the level of the single dose of the anti-TNF antibody fragment. This was either 0.1 mg/kg of body weight, 0.3 mg/kg of body weight or 1.0 mg/kg of body weight. The patients in the fourth group received a "sham therapy" (placebo) for comparison. The patients were assigned at random to one of the four therapeutic regimens with anti-TNF antibody fragment. The described therapy, which was given in addition to the standard therapy of septicemic patients, was administered as brief infusion a total of nine times (9×) at intervals of 8 hours (ie. for three days) after diagnosis (=compliance with criteria for inclusion in the study). A total of 122 patients was recruited for the study, with 34 patients being assigned to the 0.1 mg/kg dose group, 30 patients to the 0.3 mg/ kg dose group, 29 patients to the 1.0 mg/kg dose group and 29 patients to the placebo group.

It was possible to measure Il-6 serum concentrations before the start of therapy in 119 of the 122 patients. The serum levels of Il-6 were >1000 pg/ml in 36 patients and <1000 pg/ml in 83 patients.

Figure 1A:
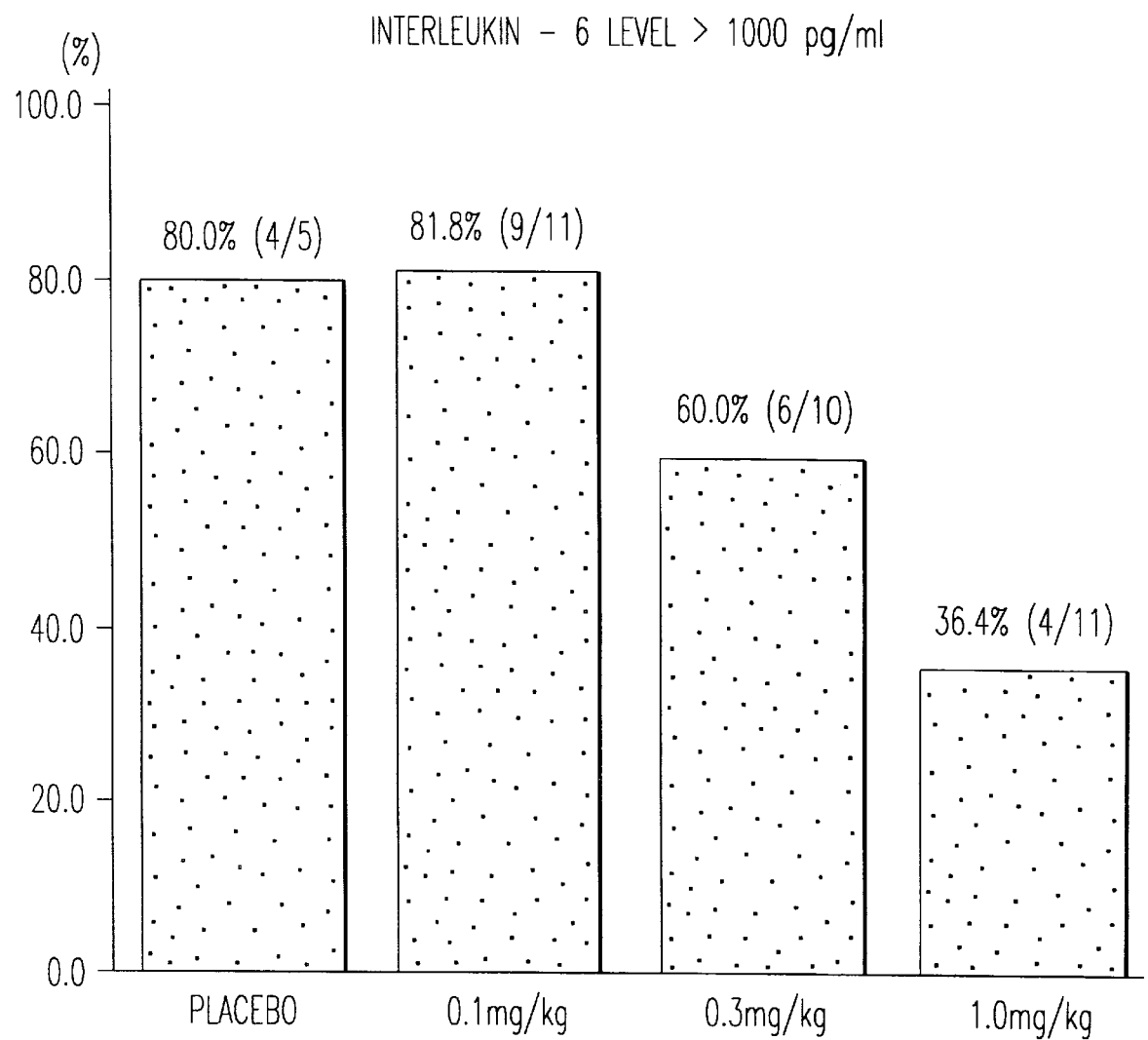
FIG. 1A shows the mortality in the population with Il-6>1000 pg/ml in the various treatment groups (placebo, 0.1, 0.3 and 1.0 mg of antibody per kg of body weight).

In the patients with Il-6>1000 pg/ml there was a dose-dependent reduction in the mortality on treatment with anti-TNF antibody fragment from 80.0% (=placebo group) to 36.4% (1.0 mg/kg antibody) (FIG. 1A).

Figure 1B:
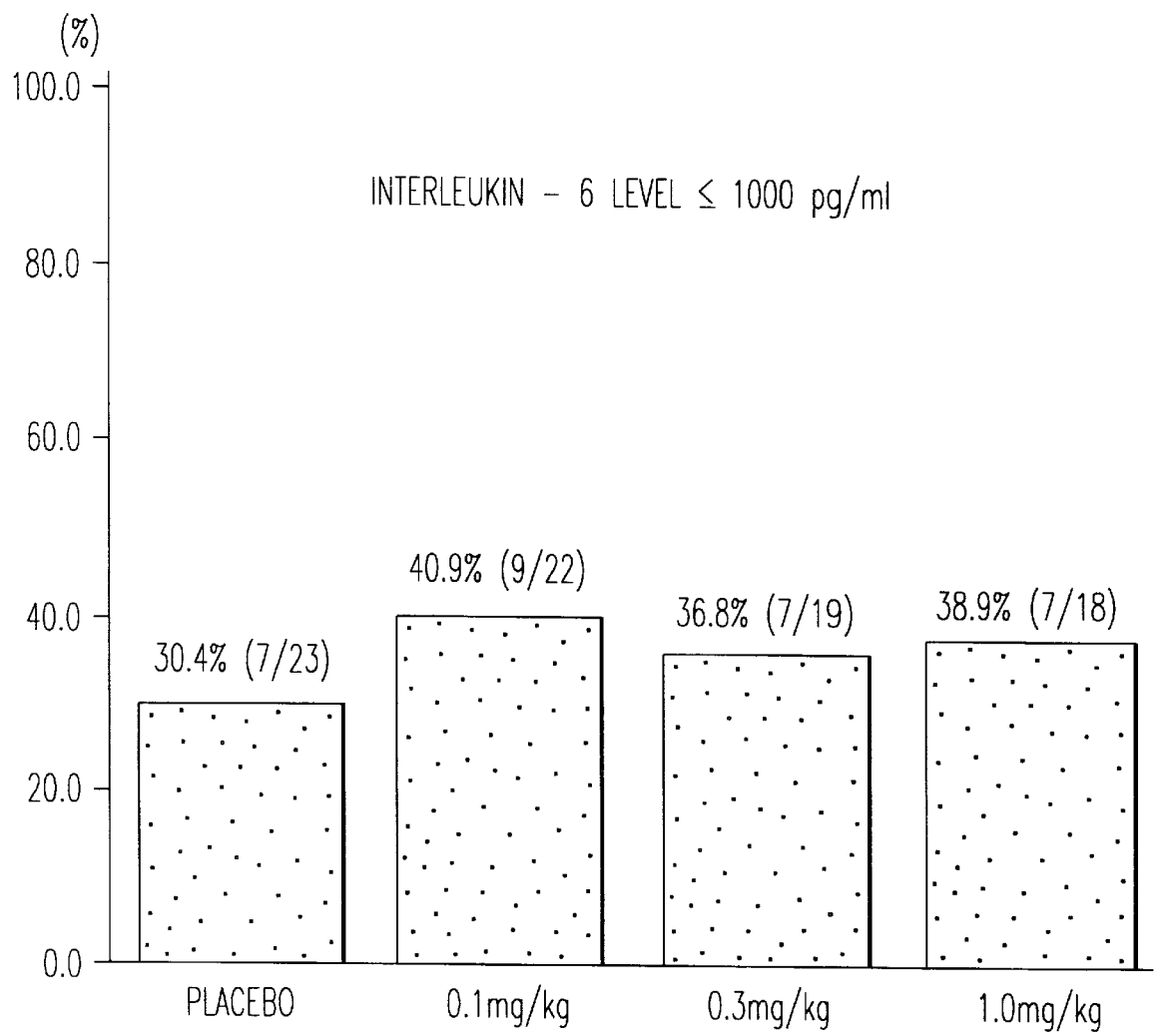
FIG. 1B shows the mortality in the population with Il-6<1000 pg/ml in the various treatment groups (placebo, 0.1, 0.3 and 1.0 mg of antibody per kg of body weight).

In the patients with Il-6<1000 pg/ml, the mortality was not reduced by treatment with anti-TNF antibody fragment, on the contrary it was slightly increased (30.4% in the placebo group compared with 38.9% in the group with 1.0 mg/kg antibody)—(FIG. 1B).

The result of this clinical study clearly proves that treatment of severe septicemia with anti-TNF antibodies is successful only when the treated septicemic patients have a serum level of Il-6>1000 pg/ml; treatment of patients with serum levels of Il-6<1000 pg/ml is unsuccessful and sometimes even contraindicated.

What is claimed is:

1. A method of treating a patient with septicemia wherein said patient has serum levels of interleukin-6 (IL-6) above 1.000 p/ml comprising:

administering a therapeutically effective amount of a tumor necrosis factor (TNF) antagonist to said patient.

2. The method of claim 1, wherein said TNF antagonist is a monoclonal anti-TNF antibody.

3. The method of claim 2, wherein said TNF antagonist is a human monoclonal anti-TNF antibody.

4. The method of claim 1, wherein said TNF antagonist is a TNF receptor or soluble fragment thereof.

* * * * *

UNITED STATES PATENT AND TRADEMARK OFFICE
CERTIFICATE OF CORRECTION

PATENT NO.    : 6,235,281 B1
DATED         : May 22, 2001
INVENTOR(S)   : Roswitha Stenzel et al.

It is certified that error appears in the above-identified patent and that said Letters Patent is hereby corrected as shown below:

Column 4,
Line 41, "1.000 p/ml" should read -- 1.000pg/ml --.

Signed and Sealed this

Second Day of April, 2002

JAMES E. ROGAN
Director of the United States Patent and Trademark Office

UNITED STATES PATENT AND TRADEMARK OFFICE
Certificate

Patent No. 6,235,281 B1                          Patented: May 22, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: is: Roswitha Stenzel, lampertheim, Germany; Martin Kaul, Neustadt, Germany; Lothar Daum, Otterstadt, Germany; Joachim Kempeni, Neustadt, Germany; Christa Raab, Dannstadt-Schauernheim, Germany; Sibylle Schaefer, Walldorf, Germany; and Jürgen Eiselstein, Weisenheim, Germany.

Signed and Sealed this Thirtieth Day of November 2004.

JEFFREY SIEW
*Supervisory Patent Examiner*
Art Unit 1642